United States Patent
Soldi

(12) 
(10) Patent No.: US 10,207,213 B2
(45) Date of Patent: Feb. 19, 2019

(54) TURBOMACHINERY FILTER CHANGE FORECASTER

(71) Applicant: Solar Turbines Incorporated, San Diego, CA (US)

(72) Inventor: Andrea Soldi, San Diego, CA (US)

(73) Assignee: Solar Turbines Incorporated, San Diego, CA (US)

( * ) Notice: Subject to any disclaimer, the term of this patent is extended or adjusted under 35 U.S.C. 154(b) by 160 days.

(21) Appl. No.: 15/408,243

(22) Filed: Jan. 17, 2017

(65) Prior Publication Data

US 2018/0200657 A1     Jul. 19, 2018

(51) Int. Cl.
*B01D 35/143*     (2006.01)
*B01D 46/00*      (2006.01)
*G01N 15/08*      (2006.01)

(52) U.S. Cl.
CPC ...... *B01D 46/0086* (2013.01); *B01D 2279/60* (2013.01); *G01N 2015/084* (2013.01)

(58) Field of Classification Search
CPC .. B01D 35/143; B01D 46/00; B01D 46/0086; B01D 2279/60; G01N 15/08; G01N 15/0826; G01N 2015/084
See application file for complete search history.

(56) References Cited

U.S. PATENT DOCUMENTS

| | | |
|---|---|---|
| 5,036,698 A | 8/1991 | Conti |
| 7,261,762 B2 * | 8/2007 | Kang ................. B01D 46/0086 116/DIG. 25 |
| 7,922,914 B1 | 4/2011 | Verdegan et al. |
| 8,534,123 B2 | 9/2013 | Herman et al. |
| 2015/0328568 A1 | 11/2015 | Verdegan et al. |
| 2015/0330857 A1 | 11/2015 | Henderson et al. |
| 2016/0116392 A1 | 4/2016 | Carpenter et al. |
| 2016/0320257 A1 | 11/2016 | Oakes et al. |

FOREIGN PATENT DOCUMENTS

| | | |
|---|---|---|
| WO | 2014179170 A2 | 11/2014 |
| WO | 2016087302 A1 | 6/2016 |

* cited by examiner

*Primary Examiner* — Nguyen Q. Ha
(74) *Attorney, Agent, or Firm* — Procopio, Cory, Hargreaves & Savitch LLP

(57) ABSTRACT

A method of monitoring a turbomachinery system is disclosed herein. The method includes measuring a pressure drop across an intake filter. The method further includes determining clog rate parameters for a clog rate of a filter area of the intake filter based on the measured pressure drop across the intake filter. The method yet further includes predicting an intake filter life cycle of the intake filter by predicting a pressure drop across the intake filter for the intake filter life cycle based on the determined clog rate parameters, and providing a recommended time to service the intake filter to an operator of the turbomachinery system based on the predicted intake filter life cycle.

20 Claims, 3 Drawing Sheets

TURBOMACHINERY FILTER CHANGE FORECASTER

TECHNICAL FIELD

The present disclosure generally pertains to turbomachinery, and is directed toward turbomachinery with a filter change forecaster.

BACKGROUND

Turbomachinery, such as gas turbine engines, can include intake filters that prevent foreign objects, such as dust and water, from entering into the intake ducting of the turbomachinery. Over time the intake filter may clog and require replacement.

International patent publication No. 2016/087,302 to C. Allegorico, et al. discloses a method for predicting the residual useful life of an air filter arrangement is described. The method comprises the following steps: providing a plurality of predetermined reference degradation curves; measuring a degradation parameter of the filter arrangement; estimating the residual useful life of the filter arrangement by comparing the predetermined reference degradation curves and an actual degradation curve defined by measured values of the degradation parameter.

The present disclosure is directed toward overcoming one or more of the problems discovered by the inventors or that is known in the art.

SUMMARY OF THE DISCLOSURE

In one aspect of the invention, a method of monitoring a turbomachinery system is disclosed herein. The turbomachinery system includes intake ducting and an intake filter for the intake ducting. In embodiments, the method includes measuring a pressure drop across the intake filter. The method also includes normalizing the measured pressure drop across the intake filter by a turbomachinery power output. The method further includes determining clog rate parameters for a clog rate of a filter area of the intake filter based on the normalized measured pressure drop across the intake filter, the clog rate parameters including a first clog parameter and an exponential clog parameter. The method yet further includes forecasting an intake filter life cycle of the intake filter by predicting a pressure drop across the intake filter for the intake filter life cycle based on the determined clog rate parameters. The method still further includes providing a recommended time to service the intake filter to an operator of the turbomachinery system based on the forecasted intake filter life cycle.

In another aspect of the invention, a system for monitoring a turbomachinery system is disclosed herein. The turbomachinery system includes intake ducting, an intake filter for the intake ducting, a controller, and a human machine interface. In embodiments, the system includes an intake pressure sensor located within the intake ducting. The system also includes one or more processors that receive an intake ducting pressure value from the intake ducting pressure sensor, determine a pressure drop across the intake filter by determining the difference between an atmospheric pressure value and the intake ducting pressure value, determine clog rate parameters for a clog rate of a filter area of the intake filter based on the pressure drop across the intake filter, the clog rate parameters including a first clog parameter and an exponential clog parameter, predict an intake filter life cycle of the intake filter by predicting a pressure drop across the intake filter for the intake filter life cycle based on the determined clog rate parameters, and provide a recommended time to service the intake filter to an operator of the turbomachinery system based on the predicted intake filter life cycle.

DETAILED DESCRIPTION

The systems and methods disclosed herein include a turbomachinery package with an intake filter and a forecaster. In embodiments, the forecaster uses the pressure drop measured across the intake filter to forecast the intake filter life cycle and to predict when to service the intake filter.

Figure 1:
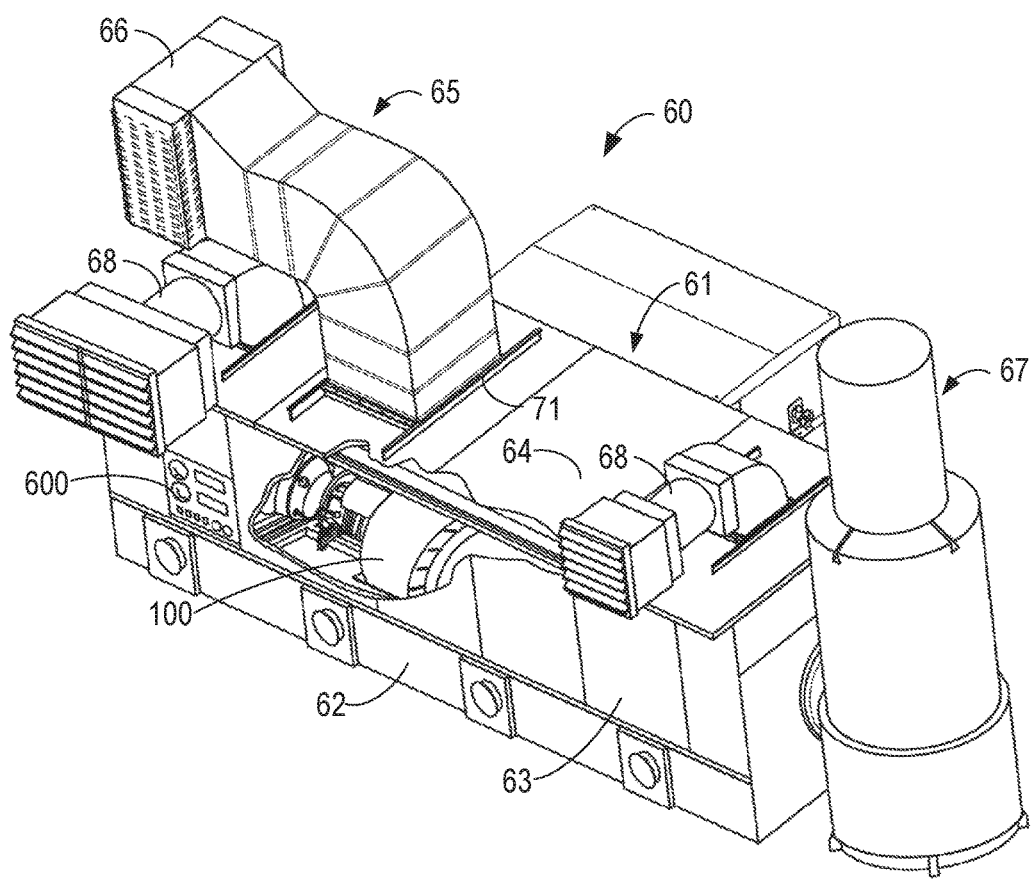
FIG. 1 is a perspective view of a turbomachinery package.

FIG. 1 is a perspective view of a turbomachinery package 60. The turbomachinery package 60 may include an enclosure 61, intake ducting 65, exhaust ducting 67, and a control system 600. The enclosure 61 may include an enclosure platform 62, enclosure walls 63, an enclosure roof 64, enclosure vents 68, and turbomachinery 100. The enclosure platform 62 may support the turbomachinery 100 including a turbomachine, such as a gas turbine engine and any driven equipment connected to the turbomachine, such as a generator or gas compressor. The enclosure platform 62 may include a lubricant tank for the turbomachinery.

The enclosure walls 63 may extend up from the enclosure platform 62 and may be formed of enclosure panels. The enclosure panels may generally be solid sheets that are joined together. The enclosure roof 64 may be joined to the enclosure walls 63. The enclosure roof 64 may include an enclosure inlet 71 therein.

The intake ducting 65 may connect to the enclosure roof 64 and to an inlet of the turbomachinery 100 at the enclosure inlet 71. The intake ducting 65 may include an intake filter 66, which may be connected to an end thereof distal to the connection to the enclosure inlet 71.

The control system 600 may monitor and control the turbomachinery 100 including the turbomachine and associated equipment, such as the driven equipment and other systems and hardware, such as the intake filter 66.

Figure 2:
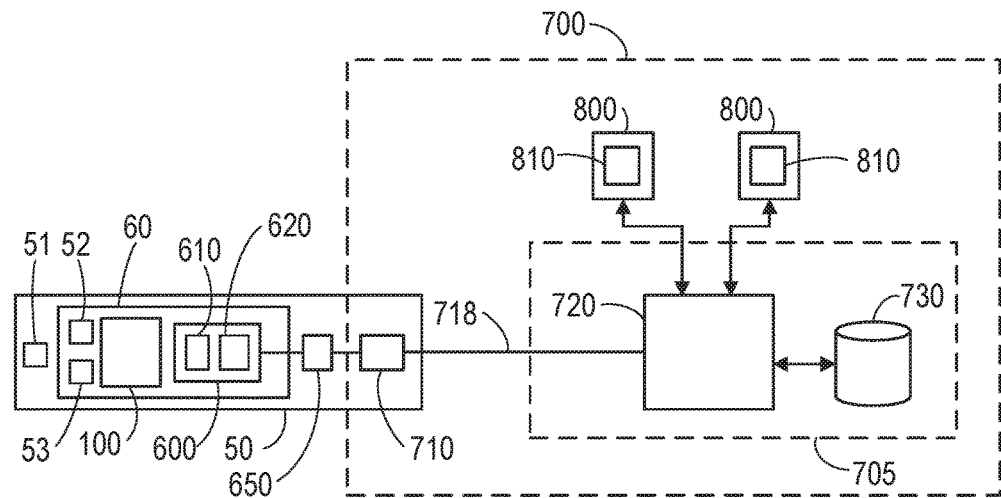
FIG. 2 is a schematic illustration of a turbomachinery system connected to a monitoring system.

FIG. 2 is a schematic illustration of a turbomachinery system 50 connected to a monitoring system 700. The turbomachinery system 50 may include a turbomachinery package 60, a firewall 650, a monitoring connection system 710, and sensors connected thereto. The sensors may include an atmospheric pressure sensor 51, an intake ducting pressure sensor 52, other pressure sensors, temperature sensors, flowmeters, and the like.

The control system 600 includes a controller 610 and a human machine interface system (HMI) 620. The controller 610 may obtain, inter alia, the data from the sensors that correspond to the measurements taken by the sensors, to monitor the turbomachinery system 50, and to control the turbomachinery system 50 based on the data obtained. The controller 610 may also monitor the turbomachinery system 50 for events, such as trigger events, alarms, and shutdowns of the turbomachinery 100.

The HMI 620 may include a high speed recorder (HSR) 630 that may obtain and log the values of the sensors and the status bits of the event types monitored by the controller 610. The HMI 620 may be connected to a monitoring connection system 710. In the embodiment illustrated, a firewall 650 is connected between the HMI 620 and the monitoring connection system 710. In other embodiments, the firewall 650 is connected between the controller 610 and the HMI 620, and between the controller 610 and the monitoring connection system 710. In these embodiments, the HMI 620 and the monitoring connection system 710 may be connected in parallel. The firewall 650 may be a read only firewall for the controller 610 to prevent remote access to the controller 610.

The monitoring system 700 may include a monitoring system server 720, a monitoring system data store 730, monitoring devices 800, and the monitoring connection systems 710 of the turbomachinery systems 50. The monitoring system server 720 may be located at a central data center 705 remote from the turbomachinery systems 50. The monitoring system server 720 may include a server or a network of servers. The monitoring system server 720 may be connected to the monitoring connection system 710 over a network. The monitoring connection system 710 may obtain data from the HMI 620, such as the sensor data and the event data from the HSR 630, and provide that data to the monitoring system server 720.

The monitoring system server 720 may receive one or more data streams 718 from the monitoring connection system 710 that may include, inter alia, data related to the various sensors of the turbomachinery system 50, such as sensors monitoring the intake filter 66, the turbomachine, and equipment associated with the turbomachine including gas compressors, gearboxes, fuel systems, batteries, lube oil, driven equipment, electric motor drives, and other systems connected to or on the turbomachinery package 60. Each data stream 718 may be a single real time data stream 718. The monitoring system server 720 may include a monitoring system data store 730 for storing the information received from the data streams 718. The monitoring system data store 730 may be a fast cache, which may allow immediate access to the data as it is stored so that the data can then be immediately be prepared for use and distribution to the monitoring devices 800.

Each monitoring device 800 may include a data viewer 810 that is configured to display the information obtained from the monitoring system server 720 to a user, such as an operator, an engineer, or owner of the turbomachinery system 50.

The atmospheric pressure sensor 51 may measure atmospheric air pressure outside of the outside of the turbomachinery package 60 on a regular interval, such as hourly, daily, or twice a day. The intake ducting pressure sensor 52 may measure the air pressure inside the intake ducting 65 on the regular interval. The atmospheric pressure sensor 51 and the intake ducting pressure sensor 52 may provide the pressure drop across the intake filter 66.

In some embodiments, the turbomachinery package 60 may also include an intake ducting flowmeter 53 that may measure the flowrate of the air through the intake ducting 65.

Figure 3:
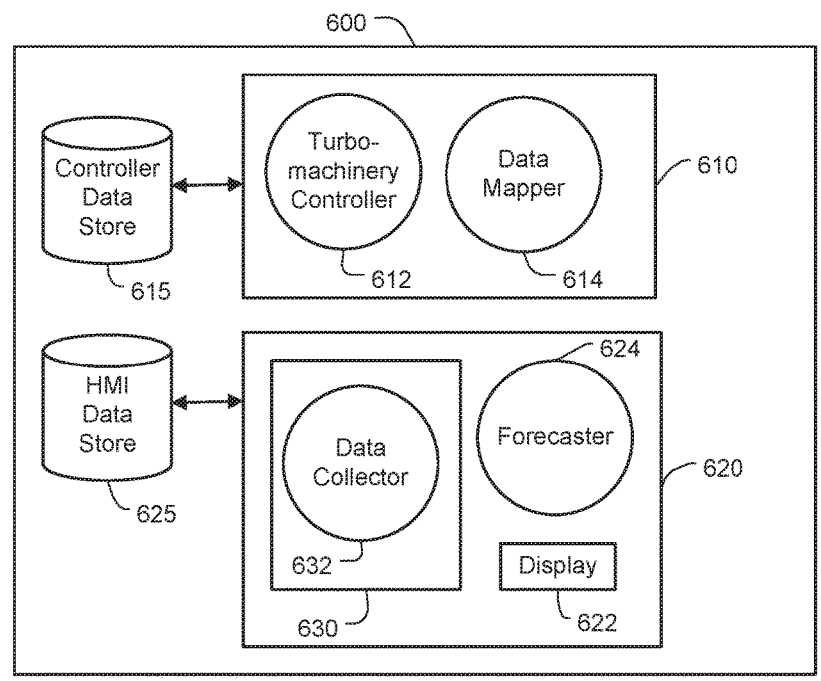
FIG. 3 is a functional block diagram of the control system of FIG. 2.

FIG. 3 is a functional block diagram of the control system 600 of FIG. 2. The controller 610 may include a turbomachinery controller 612 and a data mapper 614. The turbomachinery controller 612 is configured to control the turbomachinery system 50 during operation of the turbomachinery 100. The turbomachinery controller 612 may use the values obtained from various sensors to control the turbomachinery system 50.

The data mapper 614 may log an array related to, inter alia, each event and the values obtained from each sensor. The log may include the recorded values from the atmospheric pressure sensor 51 and the intake ducting pressure sensor 52.

The control system 600 may include a controller data store 615. The controller data store 615 may be used to store, inter alia, the most recently obtained values from sensors.

The HSR 630 may include a data collector 632. The data collector 632 may obtain, from the controller 610 and in particular the data mapper 614, the logged data including the values obtained from the atmospheric pressure sensor 51 and the intake ducting pressure sensor 52. The Data collector 632 may provide the logged data to the monitoring connection system 710 and to the forecaster 624.

The HMI 620 may also include a forecaster 624 and a display 622. The forecaster 624 determines and predicts when the intake filter 66 will need to be serviced. In some embodiments, the forecaster 624 may predict when the intake filter 66 should be replaced and when the intake filter 66 should be cleaned, such as by reversing the airflow there through. The HMI 620 may provide the prediction to an operator of the turbomachinery system 50 on the display 622. The forecaster 624 may provide the determination and prediction to the HSR 630 and in particular to the data collector 632. The HSR 630 may provide the determination and prediction to the monitoring system 700, which may facilitate providing the determination and prediction to the operator via a monitoring device 800.

INDUSTRIAL APPLICABILITY

Turbomachinery system 50 may be suited for any number of industrial applications such as various aspects of the oil and gas industry (including transmission, gathering, storage, withdrawal, and lifting of oil and natural gas), the power generation industry, cogeneration, aerospace, agricultural, mining, rail, construction, earthmoving, forestry, and other transportation industries.

During operation of a turbomachinery system 50, pollutants, such as dust and other particles, may build up in the intake filter 66, which may clog up the filter and restrict the airflow there through. The intake filter 66 may be serviced, such as cleaned or replaced, to improve airflow into the intake ducting 65. The intake filter 66 may be expensive to replace and may require shut down of the turbomachinery 100 when servicing the intake filter 66. Providing an accurate prediction of when the intake filter 66 will need to be serviced may allow an operator to schedule the maintenance well in advance and may allow for greater planning on when to shut down the turbomachinery 100 for the maintenance. Predicting when to replace the intake filter 66 based on historical data may be limited since the operating environments for turbomachinery systems 50 vary.

Figure 4:
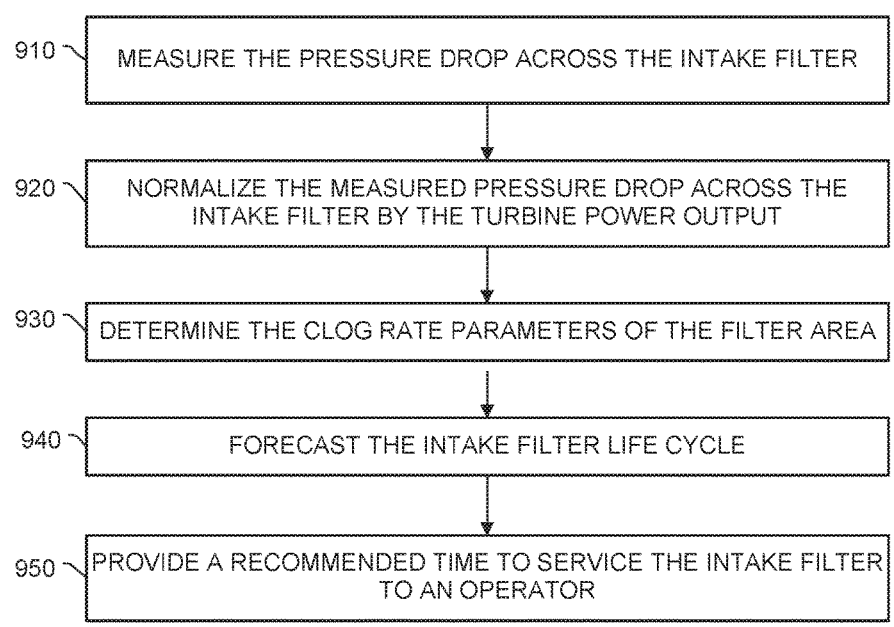
FIG. 4 is a flowchart of a method for monitoring a turbomachinery system of FIG. 1 and forecasting when to service the intake filter of FIG. 1.

FIG. 4 is a flowchart of a method for monitoring a turbomachinery system 50 of FIG. 1 and forecasting when to service the intake filter 66 of FIG. 1. The method includes measuring the pressure drop across the intake filter 66 at step 910. Step 910 may include the forecaster 624 obtaining an atmospheric pressure and an intake ducting pressure. The atmospheric pressure may be obtained using the atmospheric pressure sensor 51 or from a source external to the turbomachinery system 50. The intake ducting pressure may be obtained from the intake ducting pressure sensor 52. Step

910 may also include determining the pressure drop by determining the difference between the atmospheric pressure and the intake ducting pressure, such as by subtracting the intake ducting pressure from the atmospheric pressure. Step 910 along with the remaining steps outlined herein may be performed on an interval. The values for the intake ducting pressure and the atmospheric pressure, and/or the pressure drop across the intake filter 66 measured and determined for each interval may be stored in the HMI data store 625.

The method may also include normalizing the measured pressure drop across the intake filter 66 by the turbomachinery power output at step 920. In embodiments, step 920 includes dividing the pressure drop across the intake filter 66 by the turbomachinery power output. Step 920 may include the forecaster 624 obtaining a turbomachinery power output value of the turbomachinery 100 at the time the intake ducting pressure value was obtained from the intake ducting pressure sensor 52, such as the turbomachinery power output value obtained within a selected timeframe of obtaining the intake ducting pressure value, and the forecaster 624 determining the normalized value of the measured pressure drop across the intake filter 66 at each interval. The turbomachinery power output value may be obtained from the controller 610. The turbomachinery power output along with the amount of clog in the intake filter 66 may affect the pressure drop across the intake filter 66. Normalizing the pressure drop by the turbomachinery power output may improve the forecast of when to service the intake filter 66. The normalized pressure drop values determined at each interval may also be stored in the HMI data store 625.

The method may further include determining the clog rate parameters of the filter area at step 930. The clog rate parameters may help define the reduction in a surface area of the intake filter 66 over time. The forecaster 624 may determine the clog rate parameters using measured pressure drop values obtained during operation of the turbomachinery 100 within the lifetime of the intake filter 66, such as the pressure drops obtained since the latest service was performed on the intake filter 66. The measured pressure drop values may be normalized at step 920 prior to step 930. The clog rate parameters may be determined using the following:

$$\Delta P = \frac{1}{2}\left(\frac{\phi}{S - C(t)}\right)^2 \rho;$$

where $\Delta P$ is the pressure drop across the intake filter 66, such as the normalized pressure drop across the intake filter 66, $\phi$ is the flowrate of the air through the intake filter 66, $\rho$ is the density of the air, S is the surface area of the intake filter 66, and C(t) is the clog rate. The flowrate of the air through the intake filter 66 may be measured using the intake ducting flowmeter 53 located within the intake ducting 65 or may be taken as a constant that is determined based on the operating conditions of the turbomachinery 100. Similarly, the density of the air may be taken as a constant or may be measured using a sensor. S−C(t) may define the effective surface area of the intake filter 66.

In some embodiments, the clog rate equation C(t) may include a first clog parameter and an exponential clog parameter. The first clog parameter may account for the rate at which large particles will clog the intake filter 66. However, as the large particles begin to clog the intake filter 66, the large particles may create locations within the intake filter 66 where smaller particles may be captured, which then may capture even smaller particles, and so forth. This may result in the intake filter 66 clogging at an exponential rate, which the exponential clog parameter may account for. In other embodiments, the clog rate equation C(t) may also include a second clog parameter. The second clog parameter may act as an offset. The offset may account for the initial condition of the intake filter 66 at the beginning of the pressure drop data set used to determine the clog rate parameters, such as a clean filter, data that doesn't start from the beginning, or a partially cleaned filter.

In one embodiment, the clog rate is determined as: $C(t) = K_2 + (K_1 * \phi * t)^\gamma$; where $K_1$ is the first clog parameter, $K_2$ is the second clog parameter, $\phi$ is the flowrate of the air through the intake filter 66, t is time, and $\gamma$ is the exponential clog parameter.

In one embodiment, step 930 is performed using a genetic algorithm, where the clog rate parameters are set as chromosomes of a DNA chain in the genetic algorithm. The initial selection of values for the clog rate parameters may be completely random or may rely on the values previously determined in a previous iteration of the method. These parent values are crossed over to generate new offspring values that are mutated, with one or more of the values randomly changed. The best mutated offspring values are selected as new parent values and the process is repeated until the right clog rate parameters are found, such as the clog rate parameters that match the data set of the measured pressure drop across the intake filter 66 obtained.

The method still further includes forecasting the intake filter life cycle at step 940. Step 940 may include and be expressed as a forecast or prediction of what the pressure drop across the intake filter 66 will be over the predicted life cycle. Step 940 may include using the determined clog rate parameters to determine a prediction of the pressure drop across the intake filter 66 that will happen over a predetermined amount of time using the same formula:

$$\Delta P = \frac{1}{2}\left(\frac{\phi}{S - C(t)}\right)^2 \rho.$$

The method yet further includes providing a recommended time to service the intake filter 66 to an operator at step 950. Step 950 may include identifying when the forecasted pressure drop across the intake filter 66 will reach a predetermined amount. The predetermined amount may be an amount that signifies that the intake filter 66 will be too clogged to function properly or may be a value with a built in safety factor from when the intake filter 66 will be too clogged to function properly. The operator may be, inter alia, an owner, an engineer or a service representative. The forecaster 624 may provide the service recommendation to the HMI 620, which may display the recommendation. The forecaster 624 may also provide the information to the data collector 632, which in turn may provide the information to the monitoring system 700. The monitoring system 700 may then provide the information to the operator via the data viewer 810 on the monitoring device 800. The recommended time to service the intake filter 66 may be, inter alia, a specific time, a specific date, or may be a timeframe between times or dates.

In some embodiments, the forecaster 624 may be implemented on the monitoring system server 720. In these embodiments, the data collector 632 may provide the logged data via the package data stream 718. In these embodiments, the values for determinations made during the method, such as the intake ducting pressure and the atmospheric pressure, and/or the pressure drop across the intake filter 66 measured and determined for each interval, may be stored in the monitoring system data store 730.

Various methods disclosed herein can each be performed concurrently. For example, the HMI 620 or the monitoring device 800 can be providing the recommended time to service the intake filter 66 to an operator while the next iteration of steps 910 to 940 are being performed to update the prediction provided at step 950.

Those of skill will appreciate that the various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the design constraints imposed on the overall system. Skilled persons can implement the described functionality in varying ways for each particular application, but such implementation decisions should not be interpreted as causing a departure from the scope of the invention. In addition, the grouping of functions within a module, block, or step is for ease of description. Specific functions or steps can be moved from one module or block without departing from the invention.

The various illustrative logical blocks described in connection with the embodiments disclosed herein, such as the controller 610 including the turbomachinery controller 612 and the data mapper 614, the HMI 620 including the HSR 630, the data collector 632, the forecaster 624, the monitoring connection system 710, the monitoring system servers 740, and the monitoring device 800 including the data viewer 810, can be implemented or performed with a general purpose processor, a digital signal processor (DSP), application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any processor, controller, or microcontroller. A processor can also be implemented as a combination of computing devices, for example, a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor (e.g., of a computer), or in a combination of the two. A software module can reside in RAM memory, flash memory, ROM memory, EPROM memory, EEPROM memory, registers, hard disk, a removable disk, a CD-ROM, or any other form of storage medium readable by a processor. An exemplary storage medium can be coupled to the processor such that the processor can read information from, and write information to, the storage medium. In the alternative, the storage medium can be integral to the processor. The processor and the storage medium can reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art.

What is claimed is:

1. A method of monitoring a turbomachinery system including intake ducting and an intake filter for the intake ducting, the method comprising:
measuring a pressure drop across the intake filter;
normalizing the measured pressure drop across the intake filter by a turbomachinery power output;
determining clog rate parameters for a clog rate of a filter area of the intake filter based on the normalized measured pressure drop across the intake filter, the clog rate parameters including a first clog parameter and an exponential clog parameter;
predicting an intake filter life cycle, including predicting a pressure drop across the intake filter for an intake filter life cycle based on the determined clog rate parameters; and
providing a recommended time to service the intake filter to an operator of the turbomachinery system based on the predicted intake filter life cycle.

2. The method of claim 1, wherein the turbomachinery system includes an intake ducting pressure sensor located in the intake ducting and an intake atmospheric pressure sensor, and wherein measuring the pressure drop across the intake filter includes obtaining an intake ducting pressure value from the intake ducting pressure sensor and an atmospheric pressure value from the atmospheric pressure sensor and determining a difference between the intake ducting pressure value and the atmospheric pressure value.

3. The method of claim 1, wherein determining the clog rate parameters for the clog rate of the filter area of the intake filter based on the normalized measured pressure drop across the intake filter and predicting the pressure drop across the intake filter for the intake filter life cycle based on the determined clog rate parameters each include the pressure drop across the intake filter as the density of the air divided by two, times the square of a flowrate of air through the intake filter divided by the effective surface area of the intake filter, and the effective surface area of the intake filter is the filter area minus the clog rate.

4. The method of claim 3, wherein the clog rate parameters include a second clog parameter, and wherein determining the clog rate parameters for the clog rate of the filter area of the intake filter based on the normalized measured pressure drop across the intake filter and predicting the pressure drop across the intake filter for the intake filter life cycle based on the determined clog rate parameters each include the clog rate as the product of the first clog parameter, the flowrate and time raised to the power of the exponential clog parameter plus the second clog parameter.

5. The method of claim 3, wherein determining the clog rate parameters for the clog rate of the filter area of the intake filter based on the normalized measured pressure drop across the intake filter and predicting the pressure drop across the intake filter for the intake filter life cycle based on the determined clog rate parameters each include the flowrate as a constant.

6. The method of claim 3, further comprising measuring the flowrate with a flowmeter of the turbomachinery system located in the intake ducting.

7. The method of claim 1, wherein the steps of measuring the pressure drop across the intake filter, normalizing the measured pressure drop across the intake filter by the turbomachinery power output, determining the clog rate parameters for the clog rate of the filter area of the intake filter based on the normalized measured pressure drop across the intake filter, predicting the pressure drop across the intake filter for an intake filter life cycle based on the determined clog rate parameters and providing the recommended time to service the intake filter to an operator of the turbomachinery system are performed on an interval; and wherein the step of determining the clog rate parameters for the clog rate of the filter area of the intake filter is based on multiple normalized pressure drops obtained since the latest service was performed on the intake filter.

8. A method of monitoring a turbomachinery system including intake ducting, an intake filter for the intake ducting, a controller, and a human machine interface, the method comprising:
the controller obtaining an intake ducting pressure value from an intake ducting pressure sensor of the turbomachinery system located within the intake ducting;
a forecaster of the human machine interface determining a pressure drop across the intake filter by determining a difference between an atmospheric pressure value and the intake ducting pressure value;
the forecaster determining clog rate parameters for a clog rate of a filter area of the intake filter based on the pressure drop across the intake filter, the clog rate parameters including a first clog parameter and an exponential clog parameter;
the forecaster predicting an intake filter life cycle by predicting a pressure drop across the intake filter for the intake filter life cycle based on the determined clog rate parameters; and
the human machine interface providing a recommended time to service the intake filter to an operator of the turbomachinery system based on the predicted intake filter life cycle.

9. The method of claim 8, further comprising the forecaster normalizing the measured pressure drop across the intake filter by a turbomachinery power output prior to using the measured pressure drop across the intake filter to determine the clog rate parameters for the clog rate of the filter area of the intake filter.

10. The method of claim 8, wherein the human machine interface displays the recommended time to service the intake filter on a display of the human machine interface.

11. The method of claim 8, wherein the human machine interface providing the recommended time to service the intake filter to the operator of the turbomachinery system includes the human machine interface providing the recommended time to service the intake filter to a monitoring system, and wherein the monitoring system provides the recommended time to service the intake filter to a monitoring device of the operator.

12. The method of claim 8, wherein the turbomachinery system includes an atmospheric pressure sensor, and wherein the controller obtains the atmospheric pressure value from the atmospheric pressure sensor.

13. The method of claim 8, wherein the forecaster determining the clog rate parameters for the clog rate of the filter area of the intake filter based on the pressure drop across the intake filter and the forecaster predicting the intake filter life cycle by predicting the pressure drop across the intake filter for the intake filter life cycle based on the determined clog rate parameters each include the pressure drop across the intake filter as the density of the air divided by two, times the square of a flowrate of air through the intake filter divided by the effective surface area of the intake filter, and the effective surface area of the intake filter is the filter area minus the clog rate.

14. The method of claim 13, wherein the clog rate parameters include a second clog parameter, and wherein the forecaster determining the clog rate parameters for the clog rate of the filter area of the intake filter based on the pressure drop across the intake filter and the forecaster predicting the intake filter life cycle by predicting the pressure drop across the intake filter for the intake filter life cycle based on the determined clog rate parameters each include the clog rate as the product of the first clog parameter, the flowrate and time raised to the power of the exponential clog parameter plus the second clog parameter.

15. A system for monitoring a turbomachinery system including intake ducting, an intake filter for the intake ducting, a controller, and a human machine interface, the system comprising:
an intake pressure sensor located within the intake ducting; and
one or more processors configured to:
receive an intake ducting pressure value from the intake ducting pressure sensor,
determine a pressure drop across the intake filter by determining a difference between an atmospheric pressure value and the intake ducting pressure value,
determine clog rate parameters for a clog rate of a filter area of the intake filter based on the pressure drop across the intake filter, the clog rate parameters including a first clog parameter and an exponential clog parameter,
predict an intake filter life cycle including predict a pressure drop across the intake filter for the intake filter life cycle based on the determined clog rate parameters, and
provide a recommended time to service the intake filter to an operator of the turbomachinery system based on the predicted intake filter life cycle.

16. The system of claim 15, wherein the one or more processors are further configured to normalize the measured pressure drop across the intake filter by a turbomachinery power output prior to using the measured pressure drop across the intake filter to determine the clog rate parameters for the clog rate of the filter area of the intake filter.

17. The system of claim 15, wherein the one or more processors are configured to display the recommended time to service the intake filter on a display of the human machine interface.

18. The system of claim 15, further comprising an atmospheric pressure sensor, and wherein the one or more processors receive the atmospheric pressure value from the atmospheric pressure sensor.

19. The system of claim 15, wherein the one or more processors determining the clog rate parameters for the clog rate of the filter area of the intake filter based on the pressure drop across the intake filter and predicting the pressure drop across the intake filter for the intake filter life cycle based on the determined clog rate parameters includes the pressure drop across the intake filter as the density of the air divided by two, times the square of a flowrate of air through the intake filter divided by the effective surface area of the intake filter, and the effective surface area of the intake filter is the filter area minus the clog rate.

20. The system of claim 19, wherein the clog rate parameters include a second clog parameter, and wherein the one or more processors determining the clog rate parameters for the clog rate of the filter area of the intake filter based on the pressure drop across the intake filter and predicting the pressure drop across the intake filter for the intake filter life cycle based on the determined clog rate parameters includes the clog rate as the product of the first clog parameter, the flowrate and time raised to the power of the exponential clog parameter plus the second clog parameter.

* * * * *